United States Patent
Burkett

(12) 
(10) Patent No.: US 6,372,904 B2
(45) Date of Patent: *Apr. 16, 2002

(54) PROCESS FOR MANUFACTURE OF IN VIVO STAIN COMPOSITION

(75) Inventor: Douglas D. Burkett, Phoenix, AZ (US)

(73) Assignee: Zila, Inc., Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/759,808

(22) Filed: Jan. 11, 2001

Related U.S. Application Data

(63) Continuation of application No. 09/110,788, filed on Jul. 6, 1998, now Pat. No. 6,194,573, which is a continuation-in-part of application No. PCT/US97/20981, filed on Nov. 13, 1997.

(51) Int. Cl.[7] .............................................. C07D 279/18
(52) U.S. Cl. ........................................... 544/37; 544/34
(58) Field of Search ..................... 544/37, 34

(56) References Cited

U.S. PATENT DOCUMENTS 4,237,281 A * 12/1980 Long ........................... 544/99
4,622,395 A * 11/1986 Bellus et al. ................. 544/34
4,859,667 A * 8/1989 Lau et al. ................. 514/224.5
5,344,928 A * 9/1994 Masuya et al. ............... 544/37
5,631,371 A * 5/1997 Bloczynski ................. 544/37
6,194,573 B1 * 2/2001 Randvere et al. ............. 544/37

OTHER PUBLICATIONS

Aldrich Chemical Catalogue (p. 1203).*

* cited by examiner

Primary Examiner—Paul J. Killos
Assistant Examiner—Taylor Victor Oh
(74) Attorney, Agent, or Firm—Drummond & Duckworth

(57) ABSTRACT

A process for synthesizing 2-amino-5-dimethlyaminophenyl thiosulfonic acid comprises the step of oxidizing N,N'-dimethyl-p-phenylene-diamine in the presence of a source of thiosulfate ions, while maintaining the temperature of the reaction mixture not higher than about 10° C. This compound is useful as an intermediate in the synthesis of toluidine blue O. A process for manufacturing toluidine blue O with improved yield, includes the step of preparing the intermediate 2-amino-5-diethylaminopropyl thiosulfonic acid according to the above described procedure.

5 Claims, 1 Drawing Sheet

PROCESS FOR MANUFACTURE OF IN VIVO STAIN COMPOSITION

This application is a continuation of my U.S.A. application Ser. No. 09/110,788, filed Jul. 6, 1998, now U.S. Pat. No. 6,194,573 which was, in turn, a continuation-in-part of International Application, PCT US/97/20981, filed Nov. 13, 1997, entitled IN VIVO STAIN COMPOSITION, PROCESS OF MANUFACTURE, AND METHODS OF USE TO IDENTIFY DYSPLASTIC TISSUE.

This invention pertains to improved methods of manufacturing TBO compositions, including the novel compositions which are disclosed in my above-identified prior applications.

In another aspect, the invention concerns a method and process for manufacturing TBO compositions with improved yield, leading to manufacturing economies and increased productive capacity of the manufacturing equipment.

The various embodiments of the invention and the practice thereof will be apparent to those skilled in the art, from the following detailed description thereof, taken in conjunction with the claims and in conjunction with the drawings, in which:

BACKGROUND OF THE INVENTION

Figure 1:
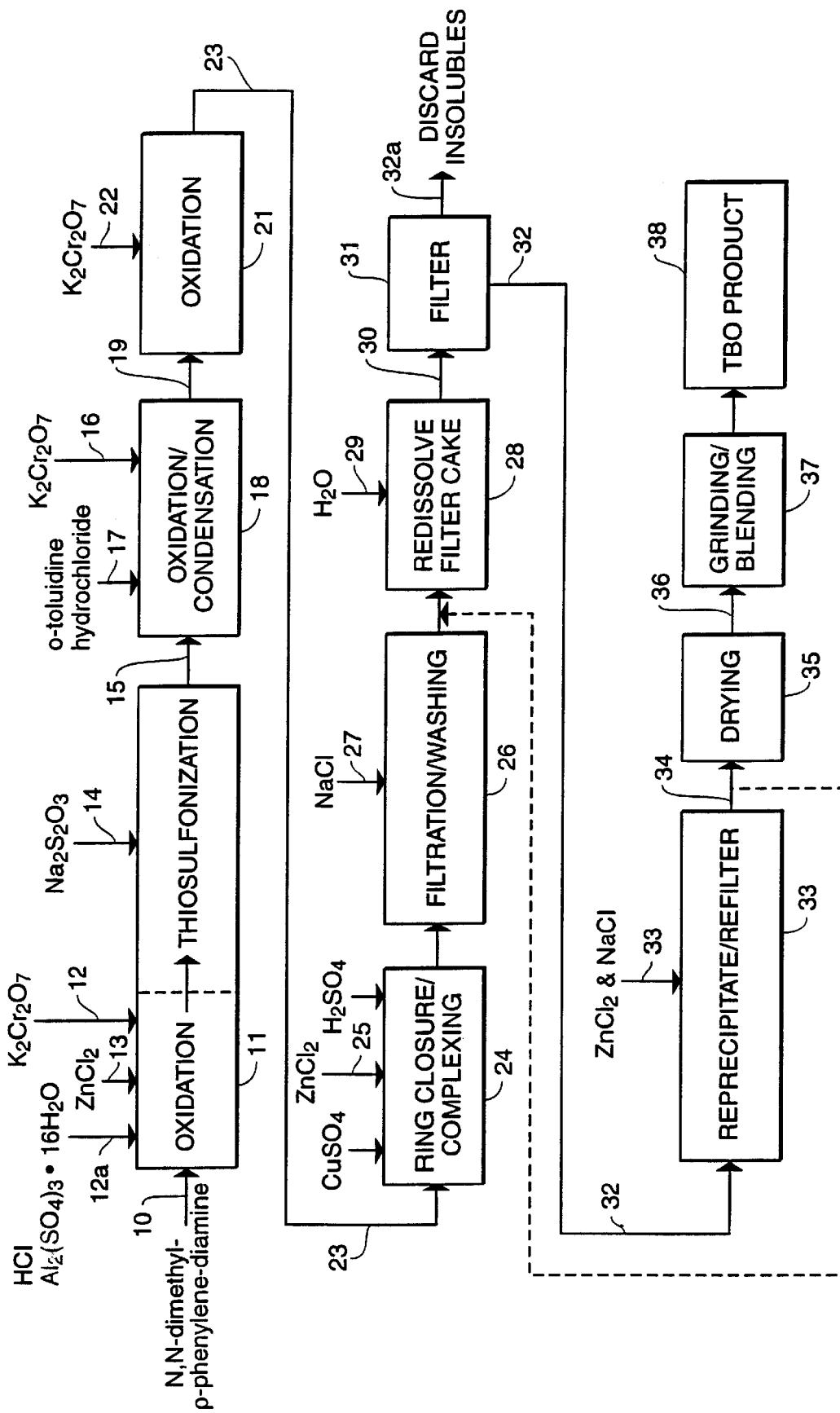
FIG. 1 is a process flow diagram, depicting the improved process which I have discovered, for manufacturing TBO products, including the novel TBO product compositions disclosed in my above-identified prior International Application.

In my prior International Application, I describe a novel general process for manufacturing a TBO product and also a process for manufacturing a TBO composition which has specific chemical characteristics, as required for regulatory approval for in vivo application to human tissue.

THE PRIOR ART

The classic synthesis of TEO, as practiced before the improvements disclosed in my above-identified International Application, is exemplified in the U.S. Pat. No. 418,055, issued Nov. 30, 1989, to Dandliker et al. This synthesis is a series of three oxidation steps: (1) oxidation of N,N-dimethyl-ρ-phenylenediamine, e.g., with potassium dichromate, to form 2-amino-5-dimethylaminophenyl thiosulfonic acid; (2) condensation of the thiosulfonic acid with o-toluidine, to form the corresponding indamine-thiosulfonic acid; and (3) ring closure of the indamine-thiosulfonic acid, e.g., in the presence of zinc chloride at boiling temperature for about 30 minutes, to form TBO. The reaction mixture is then cooled and the TBO product of the ring-closure reaction is complexed and salted out, e.g., by treatment with sodium chloride and zinc chloride, to precipitate the TBO complex, e.g., as an TBO/$ZnCl_2$ complex. Purification may be accomplished by repeated re-solution and re-precipitation, e.g., by re-solution in hot aqueous zinc chloride solution and re-precipitation with sodium chloride/zinc chloride.

In my above-identified International Application, I disclosed a novel process in which the complexing agent is added to the reaction mixture before the ring closure (third) step of the Dandliker synthesis, preferably before the first oxidation step (Step 11, of FIG. 1) of the process. The process of my prior International Application was defined as an improvement of the Dandliker process, i.e., in a process which included the steps of oxidizing N,N-dimethyl-ρ-phenylene diamine ions in a first reaction mixture to form a first intermediate, 2-amino-5-dimethylaminophenyl thiosulfonic acid, oxidizing the first intermediate and condensation of the oxidizate with o-toluidine, in a second reaction mixture, to form a second intermediate, indamine thiosulfonic acid, oxidizing the second intermediate in a third reaction mixture to close the indamine ring, forming a TBO reaction product, dissolved in the third reaction mixture, introducing a complexing reagent into said third reaction mixture, to form a TBO-complex product, and separating said TBO-complex from said third reaction mixture, the improvement on this prior art process comprising the step of adding the complexing reagent at a stage earlier than the formation of the third reaction mixture, preferably before the formation of the second reaction mixture.

In the preferred practice of the process disclosed in my prior International Application, the conversion of the starting material, N,N'-dimethy-ρ-phenylene-diamine, to form a first intermediate, 2-amino-5-dimethylaminophenyl thiosulfonic acid, was preferably carried out at a temperature of below about 10° C., and most preferably at about 5° C., for approximately 20 minutes, then warming the reaction mixture to approximately 20–25° C., then adding the thiosulfonization agent (a source of thiosulfate ions, e.g., sodium thiosulfate pentahydrate), then raising the temperature of the reaction mixture to an elevated temperature above room temperature, preferably to about 60° C. and continuing to stir the reaction mixture for approximately 30 minutes.

BRIEF DESCRIPTION OF THE INVENTION

I have now discovered that the yield of the TBO product prepared by the overall process disclosed in my prior International Application is significantly increased. The improved-yield process of the present invention is an improvement on the manufacturing process disclosed in my prior International Application, which includes the steps of oxidizing N,N'-dimethyl-ρ-phenylene diamine in a first reaction mixture, to form a first intermediate, 2-amino-5-dimethylamino thiosulfonic acid, oxidizing the first intermediate and condensing the oxidizate in a second reaction mixture with o-toluidine, forming a second intermediate, indamine thio-sulfonic acid, oxidizing the second intermediate to close the indamine ring thereof, forming a TBO-containing reaction product dissolved in a third reaction mixture, introducing a complexing agent into a reaction mixture before the formation of the third reaction mixture, to form a TBO-complex product, precipitating the TBO-complex product from the third reaction mixture and separating the TBO-complex product from the precipitate, The improvement of the present invention, for increasing the yield of TBO-complex product from the process of the present application, comprises the steps of introducing a source of thiosulfonate ions into the first reaction mixture to form the first intermediate, while maintaining the reaction mixture at a reduced temperature of about 10° C. and continuing the reaction at this reduced temperature before raising the temperature to an elevated temperature.

I have also discovered an improved process for manufacturing indamine thiosulfonic acid which comprises the steps of oxidizing N,N'-dimethyl-ρ-phenylene diamine in a reaction mixture containing it and an oxidizing agent in a reaction mixture and introducing a source of thiosulfate ions into the reaction mixture, maintaining the temperature of the oxidation-thiosulfonization reaction mixture at or below about 10° C. for approximately 30 minutes, and raising the temperature to an elevated temperature for approximately 30 minutes, to form a solution of indamine thiosulfonic acid dissolved in the reaction mixture.

DETAILED DESCRIPTION OF THE INVENTION

In the improved-yield process of the present invention, the thiosulfonization agent is introduced into the first oxidation reaction mixture at a reduced temperature of from about 5–10° C. and the reaction is continued at that reduced temperature before warming the reaction mixture to an elevated temperature of about 60° C., rather than warming the first reaction mixture to approximately 20–25° C. before introducing the thiosulfonization agent and then warming the resulting oxidization-thiosulfonization reaction mixture to the elevated temperature. After completing the thiosulfonization, the manufacturing process is continued in accordance the procedures disclosed in my prior International Application, i.e., the intermediate, 2-amino-5-dimethylaminophenyl thiosulfonic acid, is further oxidized and condensed with o-toluidine, in a second reaction mixture, forming a second intermediate, indamine thiosulfonic acid, the second intermediate is further oxidized in a third reaction mixture to close the indamine ring, forming a TBO reaction product, complexing the TBO reaction product in the third reaction mixture, forming a TRO-complex product, and separating the TBO-complex from the third reaction mixture.

Thus, in accordance with my improved-yield process, the timing of addition of the thiosulfonization agent to the first reaction mixture is changed so that it is added before the temperature of the first reaction mixture is raised in later processing steps.

Formation of First Reaction Mixture

Referring to FIG. 1, an aqueous solution of the starting material 10 is oxidized 11, preferably at less than 10° C., especially at about 5° C., by reaction with a suitable oxidizing agent 12, e.g., potassium dichromate 12, in the presence of acid, aluminum sulfate and a reagent, 13 (which is believed to complex the intermediates) and is used in a later stage of the process to complex the TBO composition components), e.g., zinc chloride. Then, before raising the temperature of the first reaction mixture, a source of thiosulfate ions 14, e.g., sodium thiosulfate, is added and the reaction is continued at such reduced temperature for approximately 30 minutes and later at an elevated temperature of about 60° C., to form a first reaction mixture 15 containing the first intermediate, 2-amino-5-dimethylaminophenyl thiosulfonic acid.

Formation of Second Reaction Mixture

The first reaction mixture 15 is then further reacted, preferably at a temperature of not greater than about 10° C., with additional oxidizing agent 16, e.g., potassium dichromate, and o-toluidine hydrochloride 17, in a condensation step 18 to form the second intermediate, a condensation product, indamine thiosulfonic acid in the second reaction mixture 19.

Formation of Third Reaction Mixture

The second reaction mixture 19 is then further oxidized 21, preferably by addition of a suitable oxidizing agent 22, e.g., potassium dichromate, at a temperature of not greater than about 10° C. This is followed by the addition of copper sulfate, zinc chloride complexing agent, acid and heating to 100° C. to effect closure of the indamine ring, forming TBO in a third reaction mixture 24. At this point the TBO is separated from the third reaction mixture and purified.

Separation/Purification of TBO

For example, in the presently preferred embodiment of the process of the present invention, the TBO is precipitated from the third reaction mixture by complexation of 24 with a suitable complexing agent 25, e.g., zinc chloride, to form the complex TBO-zinc chloride double salt. The precipitate is filtered 26 from the liquid phase and washed with sodium chloride solution 27. The washed filter cake is then redissolved 28 in a critical[1] volume of water 29 to form a TBO solution 30, which is then filtered 31 to remove undissolved solids 32a, which are discarded. Zinc Chloride, followed by a critical[2] volume/concentration of sodium chloride 33 is then added to the filtrate 32 to again precipitate the TBO-zinc chloride double salt. Then, the TBO-zinc chloride double salt is separated from the mixture by filtration, to yield a TBO-zinc chloride/TBO hydrochloride filter cake 34.

[1] If too much water is used it prevents isolation of the TBO. If too little water is used (1) all of the TBO does not get dissolved, reducing the yield and (2) it decreases the purity of the product.
[2] If too little sodium chloride is used, all of the product will not be salted out, reducing yield. If too much sodium chloride is used it will cause impurities to precipitate out along with the TBO, decreasing the purity of the product.

As indicated by the dashed line 35, the TBO filter cake 34 can be redissolved, filtered, re-precipitated and re-isolated multiple times to achieve the desired degree of purity and yield of TBO. The final purified filter cake complex product 34 is then dried 35, e.g., in conventional convection oven and/or vacuum oven and the dried filter cake 36 is ground and blended 37 to yield the final TEO product 38. The final TBO product contains both the zinc chloride double-salt of TBO (Formula X) and the chloride salt of TBO (Formulas I & II).

WORKING

EXAMPLE

The following example is presented to illustrate the practice of the invention in such terms as to enable those skilled in the art to make and use the novel TBO compositions, to practice the novel diagnostic methods using such TBO compositions and to practice the novel process for preparing TBO compositions, which together form the various embodiments of the invention, and to indicate to those skilled in the art the presently known best modes for practicing the various embodiments of the invention. These examples are presented as illustrative only and not as indicating limits on the scope of the invention, which is defined only by the appended claims.

Example 1

Manufacturing Process

This example illustrates, in the detail required to satisfy regulatory required GMP conditions, the exact procedures for carrying out the commercial scale manufacture of a batch of TBO dye product, according to the process which embodies the presently known best mode of the invention.

Preparation of Raw Materials Solutions
Equipment/Supplies:
- A. Ohaus IP15KS Balance
- B. AnD HV150KAI Balance
- C. Fairbanks H90-5150 Balance
- D. OHAUS WB25/1-20W Balance
- E. Cole Parmer (51201-30) and Thermolyne (S25535) Stirrers
- F. Sampling devices, such as steel scoops, drum samplers, etc.
- G. Erlyenmeyer flasks, beakers, carboys and other appropriate glassware.
- H. Production Solution Labels.

Safety:
Protective equipment, such as gloves, safety glasses, lab coats, and respirators should be worn when handling chemicals according to MSDS guidelines.

Raw Material Solutions Preparation Procedure:
To Hydrochloric Acid, 1364.2 g (±5.5 g) add 1364.2 g (±5.5 g) of USP Purified water. Stir until the solution is clear.

To Aluminum Sulfate Hexadecahydrate, 1779.1 g (±7.0 g) add 2548.9 g (±10.0 g) of USP Purified water. Stir until the solution is clear.

To Zinc Chloride, 7384.6 g (±30.0 g), add 2786.7 g (±11.0 g) of USP Purified water. Stir until the solution is clear.

To Potassium Dichromate, 2101.9 g (±8.0 g), add 25203.8 g (±100 g) of USP Purified water. Stir until the solution is clear.

To Sodium Thiosulfate Pentahydrate, 1526.6 g (±6.0 g), add 2043.6 g (±8.0 g) of USP Purified water. Stir until the solution is clear.

To Copper Sulfate Pentahydrate, 509.7 g (±2.0 g), add 1613.1 g (±6.0 g) of USP Purified water. Stir until the solution is clear.

To Sulfuric Acid, 600.0 g (±2.0 g), add 600.0 g (±2.0 g) of USP Purified water. Stir until the solution is clear.

To Sodium Chloride, 70.4 kg (±250 g), add 234.4 kg (±850 g) of USP Purified water. Stir until the solution is clear.

SAFETY
Protective equipment, such as gloves, safety glasses, lab coats, and respirators should be worn when handling chemicals according to MSDS guidelines.

SYNTHESIS

Synthesis Equipment and Supplies:
LFE Control Panel (3000)
gallon Jacketed Glass Lined Purification Tanks with lid (E71224)
Two 100 gallon Jacketed Glass Lined Purification Tank with lids (P1, PT-001)(P2, L-13621)
FTS Recirculating Cooler (RC96C032) and 500 gallon Cold Storage Tank (500CST)
Three Caframo Mixers (BDC-1850) (R1, 18500961)(P1, 18501148) (P2, 18501173) with shaft and impeller
Lightning Mixer (L1U08) (201550)
Three Heat Exchangers (Gardner Machinery) (R1, 01960763) (P1, 01960764) (P2, 08950727)
Three 12KW Jacket Fluid recirculators (Watlow, BLC726C3S 20)
Three Recirculation Pumps (Sta-Rite, JBHD-62S, C48J2EC15)
Masterflex Digital Peristaltic Pump (A94002806)
Masterflex Peristaltic Pump (L95003320)
Cole Parmer Peristaltic Pump (B96002074)
Neutsche Filtration unit (70-2038, 43421-1)
Two Buchner Filtration Units (Z11,624-6, Z10,441-8)
Siemens Vacuum Pump (F2BV2)
60 Gallon Glass Lined Collection Tank with lid (86854, E164-1186)
Air Compressor (DF412-2) (9502312538)
Flow Controller (3-5500) (69705069190)
Six Batch Controllers (3-5600) (#1,69705069191, #2, 69705069199, #3, 69705069194, #4, 69705058829, #5, 69705058805, #6, 69705069195)
Six Flow Sensors (#1, 69704295165, #2, 69704024995, #3, 69704024994, #4, 69704025027, #5, 69612178606, #6, 69703120990)
Four Diaphragm Pumps (M1)
Four Surge Suppressers (A301H) (#2, 15557, #3, 15561, #4, 15558, #5, 15559)
Four Air Regulators (CFR10)
Four Solenoid Valves (used with air regulators)
Four Low Flow Sensors (FS-500)
Three Solenoid Valves (EASM5V16W20)
Air Filter/Regulator (T1R)PTFE / F06R113AC
Filter media, Polypropylene (7211-1)
Filter media, Whatman Grade 52
PharMed tubing (−18, −82, −90)
pH Meter; Hanna 9321 (1303675) & Orion 620 (001911)
Spectrophotometer 20 (3MU7202070)
Fisher Scientific Vacuum Oven (9502-033)
VWR 1370 FM forced air oven (1370FM)
Dust/Mist Respirator
Thomas Wiley Laboratory Mill (3375-E10)
Patterson-Kelley Blender (Blendmaster, C416578)
OHAUS TS4KD Balance
OHAUS IP15KS Balance
Mettler AG 104 Balance
AnD HV150KA1 Balance
Fairbanks H90-5150 Balance
OHAUS AS123 Printer
OHAUS AS142 Printer
AD-8121 Multifunction Printer
Citizen iDP 3540 Dot Matrix Printer
Hewlett Packard HPLC (1050)
Ultrasonic Cleaner (8892-DTH, QCC9601 005C)
Type K Thermocouple Temperature Recorder (KTx, 6292753, 6355146)
Erlenmeyer Flasks (8L, 6 L, 4 L, 1 L)
Beakers (8L, 6L, 500 mL, 250 mL)
Carboys (4L, 10L, 50 L)
HDPE Drums (55 gallon, 100 gallon)
Volumetric Flasks (100 mL)
Plastic Funnel
Pastuer Pipettes & Bulbs and Volumetric Pipettes (10 mL, 5 mL) & Bulb
Bellows (25 mL, 50 mL)
Weigh Paper
Spatulas
Packaging Material (containers, lids, labels)
Raw Material Solutions

SYNTHESIS: Step 1

Synthesis of 2-Amino-5-Dimethylaminophenyl thiosulfonic Acid

Check the integrity of the USP water system. To the reactor add the weighed USP Grade Purified Water (28,000 g±100.0 g) and stir at 190±10 RPM. Record the conductivity of the USP water at the time the water was dispensed.

Add N,N-dimethyl-1,4-phenylenediamine (5.128 mol. 720.0 g±3.0 g). The material should be added as a powder (no lumps). Stir 10 minutes (±5 minutes).

Add hydrochloric acid (6 N, 1136.9 g±5.0 g). Stir 15 minutes (±5 minutes).

Ensure the pH meter is calibrated according to SOP # LM-007. Take a reaction mixture sample of approximately 10 mL using a plastic sampling device. Mark the sample lot #.IPS1a. Check the pH and record. The pH must be 2.8–3.8 @ 25° C.±5° C.

Add aluminum sulfate hexadecahydrate solution (4328.0 g ±21.0 g). Stir 10 minutes (±5 minutes) at 275±10 RPM.

Add zinc chloride solution (3641.5 g±18.0 g). Cool to 4° C.±1° C.

Once the temperature (PV1) is 4° C.±1° C. add potassium dichromate solution (6532.4 g±32.0 g) over a 20 minute period (±5 minutes). When addition is complete stir 20 minutes (±5 minutes) and then change the Set Point (SP1) to 25.0° C. from the Main Menu.

While maintaining the temperature at less than 10° C., add sodium thiosulfate pentahydrate solution (3570.2 g±18.0 g). Stir the solution at ~5° C. for 30 minutes (±5 minutes).

Change the Set Point to 25° C. When the temperature (PV1) reaches 25° C.±5° C., stir for 20 minutes. Change the Set Point on the LFE controller to 10.0.

Once the temperature has reached 13.0° C.±2.0° C. take a reaction mixture sample of approximately 10 mL using a plastic sampling device. Mark the sample lot #.IPS1b. Check the pH and record. The pH must be 3.1–4.1 @ 25° C.±5° C.

SYNTHESIS: Step 2
Synthesis of Indamine Thiosulfonic Acid

Weigh out o-toluidine (604.4 g±2.5 g) and cool to 18° C.±3° C. in an ice bath. Add hydrochloric acid (6 N, 1230.7 g±5.0 g) to the o-toluidine slowly. Remove the o-toluidine hydrochloride from the ice bath and allow the solution to cool to 38° C.±30° C. Add the solution to the reaction mixture and stir 5 minutes (±3 minutes).

Add potassium dichromate solution (6532.4 g±32.0 g) over a 20 minute period (±5 minutes). When addition is complete stir 10 minutes (±5 minutes).

Change the controller Set Point (SP1) to 60.0. Once the reaction mixture temperature reaches 60.0° C.±3° C. allow the mixture to stir 25 minutes (±5 minutes). A precipitate will form consisting of a green indamine.

Take a reaction mixture sample of approximately 10 mL using a pipette. Mark the sample lot #.IPS2. Record the solution color.

SYNTHESIS: Step 3
Synthesis of Toluidine Blue O and Toluidine Blue O Zinc Chloride Double Salt:

Set the LFE controller Set Point to 7.0. Once the reaction mixture temperature reaches 10.0° C.±3° C. add potassium dichromate solution (6532.4 g±32.0 g) over a 20 minute period (±5 minutes). When addition is complete stir 20 minutes.

Add potassium dichromate solution (5225.9 g±26.0 g) over a 20 minute period (±5 minutes). When addition is complete stir 20 minutes (±5 minutes).

Take a reaction mixture sample of approximately 10 mL using a pipette. Mark the sample lot #.IPS3.

Add zinc chloride solution (3641.5 g±18.0 g). Stir 20 minutes (±5 minutes) at 350±10 RPM.

Add copper sulfate pentahydrate (2122.8 g±10.0 g). Stir 15 minutes (±5 minutes).

Take a reaction mixture sample of approximately 10 mL using a pipette. Mark the sample lot #.IPS4.

Change the controller Set Point (SP1) to 100.0. Once the reaction mixture temperature reaches 67.0° C.±3° C. begin to add sulfuric acid solution to pH 2.9±0.3 by adding aliquots (500 mL, 250, 125 mL, etc.). Stir for 5 to 10 minutes after each addition and check pH.

Once the reaction mixture temperature reaches 100.0° C.±3° C. allow the mixture to stir 35±5 minutes.

Change the controller Set Point (SP1) to 35.0. Once the reaction mixture temperature reaches 70.0° C.±3° C. take a reaction mixture sample of approximately 10 mL using a pipette. Mark the sample lot #.IPS5.

Change the controller Set Point (SP1) to 2.5. Cool to 2.5° C. in 4 hours and Hold at 2.5° C.±2.0° C. for 4 to 18 hours.

Take a reaction mixture sample of approximately 10 mL using a pipette. Mark the sample lot #.IPS6. Record the solution color. Check the pH and record. Filter the sample through 0.45 micron filter paper. Take approximately 100 milligrams of the precipitate and dissolve in approximately 100 mL of HPLC water. Filter the solution through 0.45 micron filter paper. Label the solution Lot # .IPS7 and analyze the sample by the RP-HPLC Toluidine Blue O Analysis Method. See Example 3. Record the results.

Purification: Step 1

Filter the reaction mixture through suitable filter media (Whatman Grade 52).

When the reactor is empty weigh out 24.0 kg±150.0 g of 30% NaCl solution and add 24.0 kg±150.0 g of USP water (record conductivity of the dispensed water). Close the reactor bottom valve and add the 15% NaCl solution to the reactor. Stir the solution briefly. When the filtration is complete add the NaCl solution to the filtration unit to rinse the filter cake. Collect the filtrate into the same container and Label lot#.HW1 (hazardous waste 1).

Process filtrate (lot#. HW1) according to waste disposal procedures.

Check the 100 gallon glass lined, jacketed purification tank # 1 condition and make certain the tank has been properly labeled as CLEANED with date and signature. Equip the tank with a HDPE lid, Caframo stirrer, stir shaft, propeller and thermocouple probe inserted into a plastic thermocouple well. Check that the bottom valve is off and the outlet is capped.

Label the Tank with Lot#.P1A (Purification 1A).

Weigh out 190.0 kg±1.0 kg of USP water into a HDPE container (record conductivity of the dispensed water) and transfer the water to Purification Tank 1. Stir the mixture at 350 RPM. Once the NaCl wash of the filter cake is complete add the filter cake to Purification Tank 1 while stirring.

Stir the mixture 2 to 4 hours. Take a sample (through the bottom valve) of approximately 50 mL. Mark the sample lot#.IPS8. Record the solution color.

Set the Purification Tank 1 LFE controller to 75.0 (SP1).

When the mixture temperature (PV1) reaches 75.0° C.±3° C. change the Set Point on the controller to 40.0.

Allow the mixture to stir at 40° C. and 350 RPM for 12 to 36 hours.

Take a sample (through the bottom valve) of approximately 50 mL. Mark the sample lot#.IPS9. Record the solution color. Check the pH and record. Measure 1.0 mL of the sample with a 1.0 mL pipette and dilute to 100 mL in a volumetric 100 mL flask. Label the sample lot#.IPS9A. Then take 10.0 mL of this solution with a 10.0 mL pipette and dilute to 100 mL in a volumetric 100 mL flask. Label the sample lot#.IPS9B. Measure the absorbance of these samples using the spectronic 20±. Record the results. The absorbance of sample 9B should be ≧0.220.

Purification: Step 2

Filter the mixture through filter media in the filtration unit. Collect the filtrate into a Tared HDPE container with lid.

Check the 100 gallon glass lined, jacketed purification tank # 2 condition and make certain the tank has been properly labeled as CLEANED with date and signature. Equip the tank with a HDPE lid, Caframo stirrer, stir shaft, propeller and thermocouple probe inserted into a plastic thermocouple well. Check that the bottom valve is labeled as CLEANED, off (horizontal position) and the outlet is capped.

Label the Tank with Lot#.P2A (Purification 2A), date and signature.

When the filtration is complete weigh the container and solution. Subtract the tare weight. Record the solution weight. Calculate the solution volume.

(TBO soln wt. g)(100.0 mL TBO soln/100.42 g TBO soln)=ml of TBO soln

Label the filter cake lot#.HW2 (Hazardous Waste 2) and process according to waste disposal procedures.

Into a clean HDPE container weigh out a quantity of 30% NaCl solution equal to the solution volume recorded above using the following formula:

(mL of TBO soln)(116.91 g NaCl soln/100.0 mL NaCl soln)=g of NaCl soln

Sample 10 mL of the filtrate and check the pH. Label lot#.IPS10. The pH must be 3.0–4.0. Transfer the filtrate (by weight) to Purification Tank 2. Stir the solution at 350 RPM.

Add zinc chloride solution (1636.3 g±6.5 g)

Transfer the NaCl solution (by weight) to Purification Tank 2.

Set the Purification Tank 2 LFE controller to 75.0 (SP1).

When the mixture temperature (PV1) reaches 75.0° C.±3° C. change the Set Point on the controller to 5.0.

Cool to 5° C. in 6 hours and Hold at 50° C.±4.0° C. for 4 to 24 hours.

Take a sample (through the bottom valve) of approximately 50 mL. Mark the sample lot#.IPS11.PT2.

PROCESSING i. Filter

Filter the mixture through tared filtration media (Whatman Grade 52) in the filtration unit Weigh out 12 kg±50 g of 30% sodium chloride solution and dilute with 12 kg±50 g of USP water (record conductivity of the dispensed water). Wash the filter cake with the 15% sodium chloride solution by adding the solution directly to the buchner. When the filtration is complete carefully remove the filter paper containing the toluidine blue O product.

Process Lot#.HW3 (Hazardous Waste 3) according to waste disposal procedures.

ii. Dry

Place the TBO product in the oven and dry at 50.0° C.±3.0° C. for 5±1 hours. Label the oven lot#.PRE-DRY.

Remove the product from the forced air oven and place in the Vacuum Oven. Dry at 45.0° C.±3.0° C. @ 28⋇ Hg±2⋇ Hg for 10±2 hours. Label the oven lot#.DRY.

iii. Weigh

Remove the product and weigh the Toluidine Blue O and filter. Subtract the filter weight and record the TBO weight.

Using a stainless steel spatula carefully remove the product from the filter paper. Wear a Dust/Mist respirator. Weigh the Toluidine Blue.

iv. Grind

Transfer the product to the TOLUIDINE BLUE O FINISHING AREA. Check the Thomas Wiley Laboratory Mill condition and make certain the mill has been properly labeled as CLEANED with date and signature. Use the 0.5 mm screen. Attach a clean container to the delivery chute. The chamber door must be closed and latched.

Close the sliding shutter at the bottom of the hopper, remove the hopper lid and add the sample. Replace the hopper lid. Turn the mill ON and open the sliding shutter slightly. Feed sample into the mill chamber slowly enough so that the mill does not slow down or become jammed.

Once the grinding is complete carefully remove the mason jar from the delivery chute.

v. Blend

Check the Patterson-Kelly Lab Blender condition and make certain the blender has been properly labeled as CLEANED with date and signature.

Transfer the Toluidine Blue O product to the blender container and close the lid. Set the timer to 15 minutes vi. Test Sample the product for testing. Analyze the sample by the RP-HPLC Toluidine Blue O Analysis Method. Record the results.

Having described my invention in such terms as to enable persons skilled in the art to understand the invention and practice it, and, having identified the presently preferred embodiments thereof, I claim:

What is claimed is:

1. In a process for manufacturing toluidine blue O ("TBO"), which process includes the steps of:

oxidizing N,N'-dimethly-ρ-phenylene diamine in a first reaction mixture, introducing a source of thiosulfate ions into said first reaction mixture, to form a first intermediate, 2-amino-5-dimethylaminophenyl thiosulfonic acid, further oxidizing and condensing said first intermediate with o-toluidine, to form a second intermediate, indamine-thiosulfonic acid, further oxidizing said second intermediate to close the indainine ring thereof, to form a TBO-containing reaction product in a third reaction mixture, and separating the TBO-containing reaction product from the third reaction mixture, the improvement comprising the step of adding potassium dichromate as the oxidation agent of N,N-dimethyl-ρ- phenylenediamine to form 2-amino-5-dimethylaminophenyl thiosulfonic acid.

2. In a process for manufacturing toluidine blue O ("TBO"), which process includes the steps of:

oxidizing N,N'-dimethly-ρ-phenylene diamine in a first reaction mixture, introducing a source of thiosulfate ions into said first reaction mixture, to form a first intermediate, 2-amino-5-dimethylaminophenyl thiosulfonic acid, further oxidizing and condensing said first intermediate with o-toluidine, to form a second intermediate, indamine-thiosulfonic acid, further oxidizing said second intermediate to close the indamine ring thereof, to form a TBO-containing reaction product in a third reaction mixture, and separating the TBO-containing reaction product from the third reaction mixture, the improvement comprising the step of adding sodium thiosulfate pentahydrate as the thiosulfonization agent before further oxidizing and condensing said first intermediate with o-toluidine, to form a second intermediate, indamine-thiosulfonic acid.

3. In a process for manufacturing toluidine blue O ("TBO"), which process includes the steps of:

oxidizing N,N'-dimethly-ρ-phenylene diamine in a first reaction mixture, introducing a source of thiosulfate ions into said first reaction mixture, to form a first intermediate, 2-amino-5-dimethylaminophenyl thiosulfonic acid, further oxidizing and condensing said first intermediate with o-toluidine, to form a second intermediate, indamine-thiosulfonic acid, further oxidizing said second intermediate to close the indamine ring thereof, to form a TBO-containing reaction product in a third reaction mixture, and separating the TBO-containing reaction product from the third reaction mixture, the improvement comprising the step of adding zinc chloride to facilitate ring closure of the indamine-thiosulfonic acid and to form TBO.

4. In a process for manufacturing toluidine blue O ("TBO"), which process includes the steps of:

oxidizing N,N'-dimethly-ρ-phenylene diamine in a first reaction mixture, introducing a source of thiosulfate ions into said first reaction mixture, to form a first intermediate, 2-amino-5-dimethylaminophenyl thiosulfonic acid, further oxidizing and condensing said first intermediate with o-toluidine, to form a second intermediate, indamine-thiosulfonic acid, further oxidizing said second intermediate to close the indamine ring thereof, to form a TBO-containing reaction product in a third reaction mixture, and separating the TBO-containing reaction product from the third reaction mixture, the improvement comprising the steps of:
  (a.) adding potassium dichromate as the oxidation agent of N,N-dimethyl-ρ-phenylenediamine to form 2-amino-5-dimethylaminophenyl thiosulfonic acid;
  (b.) adding sodium thiosulfate pentahydrate as the thiosulfonization agent before further oxidizing and condensing said first intermediate with o-toluidine, to form a second intermediate, indamine-thiosulfonic acid; and
  (c.) adding zinc chloride to facilitate ring closure of the indamine-thiosulfonic acid and to form TBO.

5. In a process for manufacturing toluidine blue O ("TBO"), which process includes the steps of:

oxidizing N,N'-dimethly-ρ-phenylene diamine in a first reaction mixture, introducing a source of thiosulfate ions into said first reaction mixture, to form a first intermediate, 2-amino-5-dimethylaminophenyl thiosulfonic acid, further oxidizing and condensing said first intermediate with o-toluidine, to form a second intermediate, indamine-thiosulfonic acid, further oxidizing said second intermediate to close the indamine ring thereof, to form a TBO-containing reaction product in a third reaction mixture, and separating the TBO-containing reaction product from the third reaction mixture, the improvement comprising at least one step selected from the group consisting of the following steps:
  (a.) adding potassium dichromate as the oxidation agent of N,N-dimethyl-ρ-phenylenediamine to form 2-amino-5-dimethylaminophenyl thiosulfonic acid;
  (b.) adding sodium thiosulfate pentahydrate as the thiosulfonization agent before further oxidizing and condensing said first intermediate with o-toluidine, to form a second intermediate, indamine-thiosulfonic acid; and
  (c.) adding zinc chloride to facilitate ring closure of the indamine-thiosulfonic acid and to form TBO.

* * * * *